Figure 1:
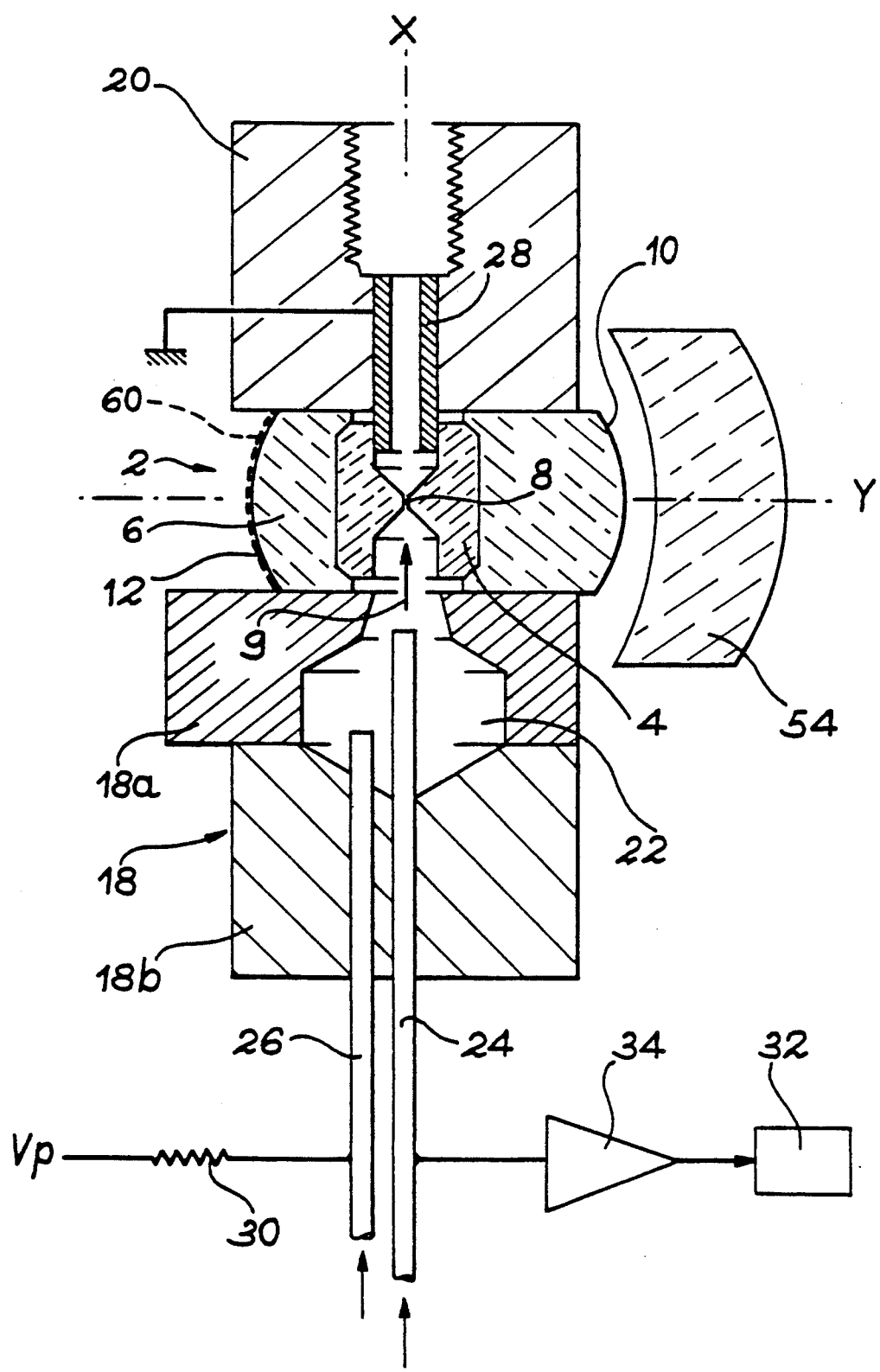

United States Patent [19]

Gaucher et al.

[11] Patent Number: 4,997,275
[45] Date of Patent: Mar. 5, 1991

[54] PROCESS FOR THE PRODUCTION OF A DEVICE FOR THE OPTICAL ANALYSIS OF A MICROPARTICLE FLUX AND APPLICATION TO THE PRODUCTION OF A CYTOFLUORIMETER

[75] Inventors: Jean-Claude Gaucher, le Val Saint Germain; Alain Seigneur, Choisel, both of France

[73] Assignee: Commissariat a l'Energie Atomique, Paris, France

[21] Appl. No.: 248,913

[22] Filed: Sep. 23, 1988

[30] Foreign Application Priority Data

Sep. 30, 1987 [FR] France .................... 87 13515

[51] Int. Cl.[5] ............................................ G01N 15/10
[52] U.S. Cl. ...................................... 356/72; 356/246
[58] Field of Search ............... 356/72, 73, 317, 246; 250/461.2

[56] References Cited

U.S. PATENT DOCUMENTS

| | | | |
|---|---|---|---|
| 4,348,107 | 9/1982 | Leif | 356/72 |
| 4,673,289 | 6/1987 | Gaucher | 356/72 |
| 4,790,653 | 12/1988 | North | 356/73 |

FOREIGN PATENT DOCUMENTS 0165868 12/1985 European Pat. Off. .

OTHER PUBLICATIONS

Japan Plastics Age, vol. 23, No. 201, Jan./Feb. 1985, pp. 31-34, Tokyo, JP: S. Matsuda, et al: "Plastics Lens by Injection and Compression Molding".
Patent Abstracts of Japan, vol. 7, No. 199 (M-240)[1344], Sep. 3, 1985; & JP-A-58 98 225 (Hitachi Seisakusho K.K.) 11-06-1983.
Patent Abstracts of Japan, vol. 9 No. 14 (M-352) [1737], Jan. 22, 1985; & JP-A-59 162 025 (Konishiroku Shashin Kogyo K.K.) 12-09-1984.

Primary Examiner—Richard A. Rosenberger

[57] ABSTRACT

Process for the production of a device for the optical analysis of a microparticle flux and application to the production of a cytofluorimeter.

As microparticles are able to emit light, around a nozzle (4) made from a material transparent to said light and whose hole (8) is provided for the passage of the flux, is moulded an optical element (6) made from a material transparent to said light, which has a melting point below that of the material of the nozzle and which has an optical index close to that of said material, and which has a dioptric element (10) admitting an optical axis passing through the hole. The cytofluorimeter in particular incorporates the device (2) obtained by this process.

13 Claims, 3 Drawing Sheets

PROCESS FOR THE PRODUCTION OF A DEVICE FOR THE OPTICAL ANALYSIS OF A MICROPARTICLE FLUX AND APPLICATION TO THE PRODUCTION OF A CYTOFLUORIMETER

The present invention relates to a process for the production of a device for the optical analysis of a microparticle flux.

The term "microparticles" is understood to mean animal or vegetable biological cells, or subcellular elements, such as chromosomes.

The process according to the invention more particularly applies to the production of a cytofluorimeter.

Microparticle flux optical analysis devices are already known from U.S. Pat. No. 4,348,107 and U.S. Pat. No. 4,673,289 (the latter corresponding to French patent application No. 8409676 of 20.6.1984). However, none of these documents describes a production process for such devices, which is sufficiently simple and economic to lead to devices at a reasonable cost permitting the production the certain analysis systems, e.g. simplified flux cytofluorimeters not having an excessive cost.

Numerous biological analysis laboratories will have an increasing need for such cytofluorimeters for carrying out routine analyses, in hematology or in the agro-alimentary field (particularly for the analysis of milk).

The present invention specifically relates to a process for the production of a device for the optical analysis of a microparticle flux, which is simple and leads to reasonably priced equipment.

More specifically, the present invention relates to a process for the production of a device for the optical analysis of a microparticle flux able to emit light, characterized in that around the nozzle formed from a material transparent to said light and whose hole is provided for the passage of the flux, is moulded an optical element formed from a material transparent to said light, with a melting point below that of the material of the nozzle and with an optical index close to that of said material and which has a dioptric element admitting an optical axis passing through said hole.

Preferably, in order to yet further reduce the cost of the device, the material from which the optical element is made is a plastics material and said optical element is moulded by injection. Preferably, the dioptric element is spherical and convex. Preferably, the first Weierstrass point of the spherical dioptric element coincides with the centre of the hole. This leads to an optics with a large numerical aperture, which can be followed by an optics with a smaller aperture without introducing spherical aberrations.

The use of a spherical convex dioptric element in the device helps to give it a high collection efficiency, but preferably, in order to increase this efficiency, the optical element has, opposite to the spherical dioptic element with respect to the hole, a spherical convex wall centred on the hole and after producing the device, said wall is made optically reflecting.

The nozzle used can be a commercially available nozzle, such as a sapphire perforated with a calibrated orifice. However, according to a special embodiment of the invention, the nozzle is formed beforehand by cutting a capillary tube, whilst making along the axis of the section obtained two bores with substantially conical bottoms and leaving a portion of the capillary, said portion consequently consequently constituting the said hole and converging towards said portion.

The invention also relates to the optical analysis device obtained by the inventive process and its application to a cytofluorimeter comprising the assembly of a device for the optical analysis of a microparticle flux, such as biological cells or subcellular elements, which can emit light when subject to a light or luminous excitation, the flux being directed along an axis, means for forming an exciting light beam for said microparticles and means for analyzing said light, in which the device is produced beforehand by the aforementioned inventive process.

After manufacturing the optical analysis device, the latter can be rendered integral with a part having a cavity communicating with the hole of the nozzle, said part being rendered integral with first and second tubes, whereof the respective ends issue into said cavity facing the nozzle, the first tube being provided for the circulation of a microparticle suspension in the direction of said hole, the end of the second tube being further from the hole than the end of the first tube and the second tube being provided for the circulation of a liquid intended to sheath the microparticle suspension prior to the passage thereof through the hole.

The two tubes can be electrically conductive and connected to means for electrically analyzing the cells (COULTER type measurements). In this case, preferably the device provided with said part and the tubes is oriented in such a way that the tubes are substantially vertical and positioned lower than the device. The cell flux is then oriented from bottom to top. This makes it possible to eliminate air bubbles on putting the cytofluorimeter into operation and the filling of the bore positioned above the nozzle, i.e. the electrical contact with a return electrode also provided for a COULTER type measurement.

It is also possible to orient the device provided with said part and the tubes, in such a way that these tubes are substantially vertical and positioned higher than the device. The flux of cells is then oriented from top to bottom. This procedure is necessary in a cytofluorimeter used for sorting or classifying biological cells.

Finally, in a special construction, the exciting light beam formation means have means for focussing the same and on the optical analysis device is provided an inlet face for said light beam positioned so as to permit the emission of the focussed beam into said hole perpendicular to the optical axis of the dioptic element and to the axis of the microparticle flux.

It is then possible to provide on said device, opposite to the inlet face with respect to the said hole, an outlet face for the light and position facing said outlet face a means for stopping the exciting beam, following the interaction of the latter with the micro-particle flux, said stopping means permitting the passage on either side of itself of a light diffused under small angles by the microparticles.

The invention is described in greater detail hereinafter relative to non-limitative embodiments and the attached drawings, wherein show:

FIG. 1 A diagrammatic, partial view of a cytofluorimeter having a device produced by a process according to the invention.

Figure 2:
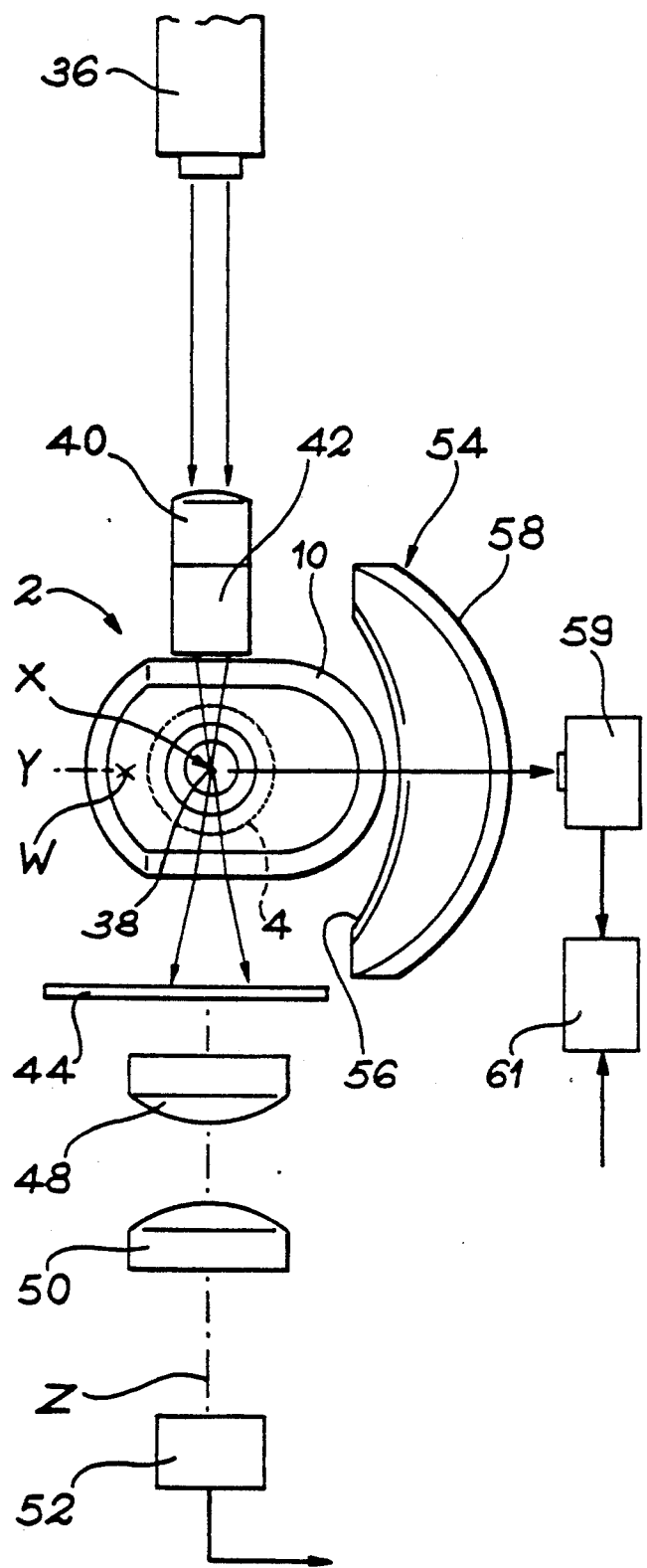

FIG. 2 A diagrammatic, partial plan view of the cytofluorimeter of FIG. 1.

Figure 3:
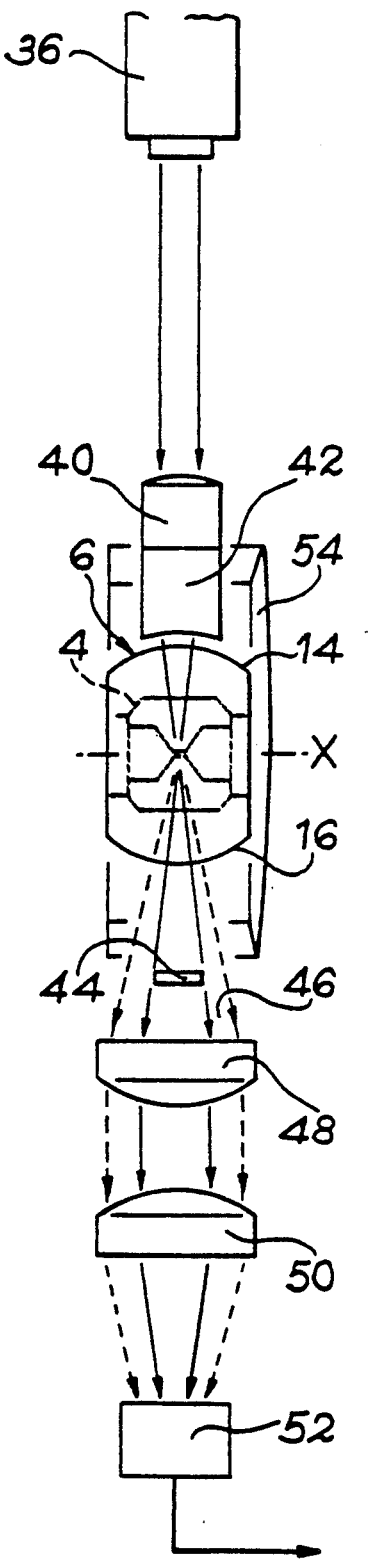

FIG. 3 A partial, diagrammatic side view of said cytofluorimeter.

Figure 4:
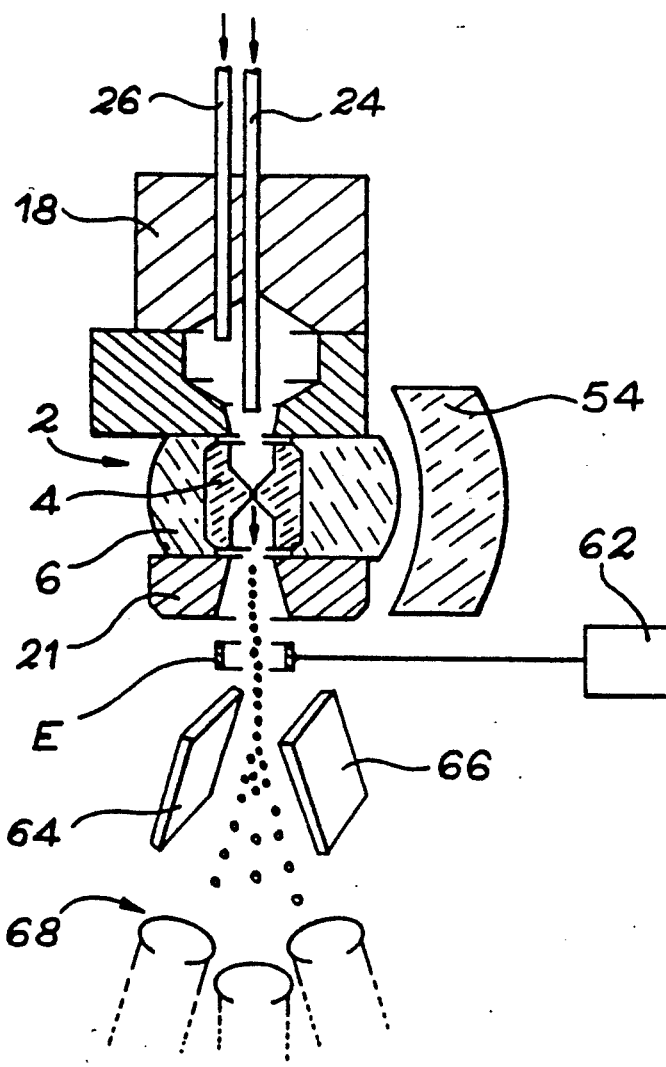

FIG. 4 A partial, diagrammatic view of another cytofluorimeter having a device obtained by a process according to the invention.

Figure 5:
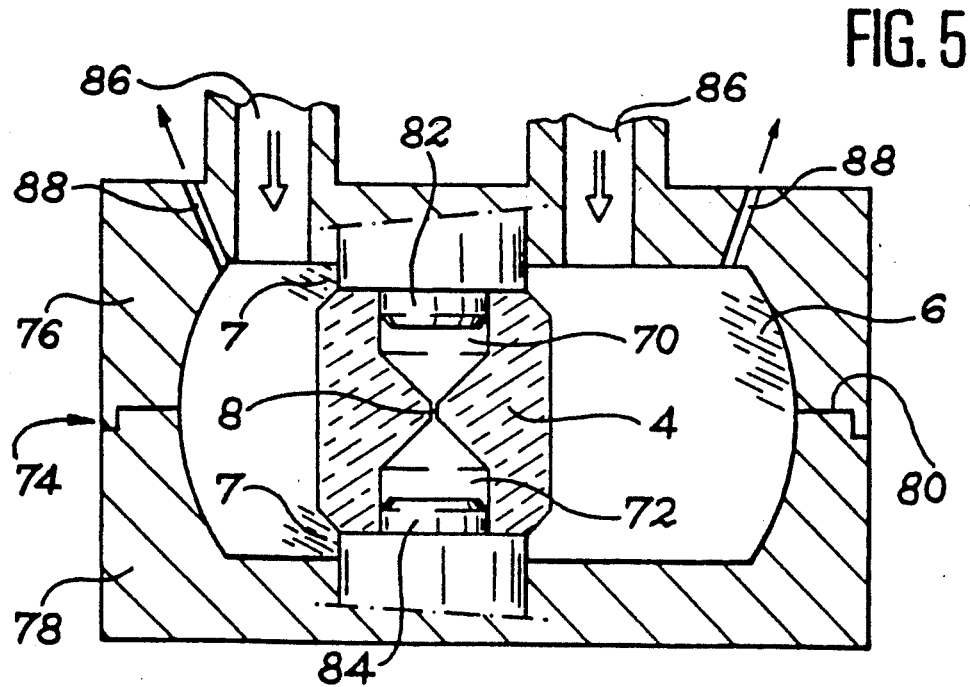

FIG. 5 Diagrammatically a process according to the invention making it possible to produce the device used in the cytofluorimeter shown in FIG. 1.

FIG. 1 diagrammatically and partially shows a cytofluorimeter having an optical analysis device 2 obtained by a process according to the invention. Around a nozzle 4, said device has a light collecting optical element 6. The nozzle 4 has an e.g. cylindrical hole or orifice 8, with a vertical axis X and intended for the passage of a flux 9 of biological cells which it is wished to study by means of the cytofluorimeter and which is directed along the axis X.

The light collection element 6, particularly of the fluorescent light emitted by the cellular flux, is limited at the top and bottom by two horizontal, planar faces. On either side of hole 8, the nozzle has two bores respectively issuing onto the said faces. Between these faces the element is limited by first 10 and second 12 convex spherical dioptric elements having the same horizontal axis of symmetry Y passing through the centre of hole 8 and by two faces 14, 16 (cf. FIG. 3), which are symmetrical with respect to one another relative to the plane defined by axes X and Y and constituting portions of a cylinder of revolution of axis Y.

The single nozzle device 2 is maintained between the respective planar faces of a lower part 18 and an upper part 20, which are electrically insulating. The lower part 18 results from the assembly of two portions 18a, 18b provided so that, after assembly, part 18 has a cavity 22 issuing on to the upper face of said part 18 facing the lower bore of nozzle 4. Part 18 is rendered integral with a first tube 24, which is disposed along axis X and whereof one end issues into cavity 22 and is located in the vicinity of the upper face of part 18. Part 18 is also rendered integral with a second tube 26 parallel to tube 24 and whereof one end also issues into cavity 22, but which is further from the upper face of part 18 than the end of tube 24.

Tube 24 permits the circulation of a suspension of biological cells in the direction of nozzle 4 and tube 26 makes it possible to introduce into the chamber 22 an entraining liquid for forming a liquid sheath around the cellular suspension from tube 24.

The upper part 20 is provided with a third tube 28 of axis X communicating with the upper bore of nozzle 4 and which permits the discharge of the cellular flux out of the cytofluorimeter (e.g. into a not shown container).

The cytofluorimeter shown in FIG. 1 is more particularly intended for carrying out COULTER type electrical measurements in order to electrically count the number of cells and electrically measure the volume thereof. For this purpose, tubes 24, 26 and 28 are electrically conductive and are e.g. made from a metal such as platinum. Tubes 26 and 28 permit the electrical polarization of hole 8 of nozzle 4. A polarizing potential Vp is applied to tube 26 via an appropriate electrical resistor 30 and tube 28 is earthed. Tube 24 is connected to appropriate electronic measuring means 32 via a preamplifier 34 for supplying an electrical signal representing the cellular volume.

In the cytofluorimeter shown in FIG. 1, the cellular flux is oriented from bottom to top, which is preferable to the reverse orientation, so as to ensure the elimination of air bubbles on putting the cytofluorimeter into operation and so as to permit a good contact of the tube 28, forming an upper electrode, with the liquid filling the upper bore.

The optical excitation of the cellular flux is obtained by an appropriate light source 36, preferably a laser, whose beam is directed towards the face 14 or inlet face, in accordance with an axis Z perpendicular to axes Y and X. The laser beam is focussed on the centre 38 of the hole of nozzle 4 in order to intercept the cell flux. In practice, the hole is a microhole which substantially coincides with its centre 38.

The laser beam is focussed by means of a focussing lens 40 coupled to a cylindrical lens 42 making it possible to obtain an elliptical focussing in order to illuminate the cellular flux in a homogeneous manner. It can be seen that the cylindrical lens 42 has a cylindrical face facing the inlet face 14 and whose generatrix is parallel to the latter.

Facing face 16 or the outlet face of the laser beam is arranged a mask 44 in the form of a rectangular plate, which is elongated in accordance with the Y axis and narrow in accordance with the X axis. This mask absorbs the laser beam which has traversed device 2, whilst permitting the passage on either side of the sides of said mask and which are parallel to axis X, the light 46 diffused by the cells under small angles with respect to the laser beam axis Z. Said light 46 is focussed by means of appropriate lenses 48, 50 on to a photodetector 52, which thus supplies a signal representative of the diffusion parameter at small angles.

Another optical element 54 corresponding to element 10 in U.S. Pat. No. 4,673,289 referred to hereinbefore is positioned facing the spherical convex dioptric element 10. Element 54 is defined by a first spherical concave dioptric element 56 and by a second spherical convex dioptric element 58 admitting a common axis of symmetry coinciding with axis Y. Dioptric element 56 directly faces dioptric element 10.

Preferably, to avoid spherical aberrations, the first Weierstrass point of the dioptric element 10 coincides with the centre 38 of the nozzle hole and the second Weierstrass point of said dioptric element 10 constitutes both the centre of the first dioptric element 56 and the first Weierstrass point of said second dioptric element 58.

In order to increase the collection efficiency of the optical element 6, dioptric element 12 is coated with a metal coating 60, e.g. of aluminium (FIG. 1), in order to reflect back to the dioptric element 10 the light rays emitted in the direction of dioptric element 12. A not shown portion of the latter can be non-metallized and thus constitutes a window making it possible to observe the interior of device 2 during the regulation of the cytofluorimeter.

In known manner, the light from optical element 54 is then supplied, by not shown optical means, to photodetection means 59 and the cytofluorimeter is provided with processing means 61 which, on the basis of signals supplied by the different photodetection means thereof, make it possible to carry out the desired analyses (cf. e.g. U.S. Pat. No. 4,673,289).

FIG. 4 diagrammatically and partly shows another cytofluorimeter also having the optical analysis device 2. This cytofluorimeter makes it possible to sort the cells of the cellular flux, but does not permit the carrying out of electrical measurements of the COULTER type.

In the cytofluorimeter shown in FIG. 4, the cellular flux circulates form top to bottom. To this end, the assembly of components 2, 18, 26, 24 of the cytofluorimeter of FIG. 1 is reversed (having undergone a rotation of 180° about axis Y), the tube 28 is eliminated, part 20 is replaced by a small thickness part 21 traversed by a hole communicating with the bore of nozzle 4, which is at present at the bottom. Thus, the cell flux passes into the open air as soon as it has cleared the nozzle orifice. It is then broken up into droplets by known, not shown ultrasonic means.

The cytofluorimeter shown in FIG. 4 also has electronic means 62 for controlling the charge of these drops and the sign of said charge via an annular electrode E located in the open air facing the lower outlet of part 21, so that it can be traversed by the drops and as a function of the signals received by the different not shown photodetector means of the cytofluorimeter, which serve to detect the fluorescent light emitted by the appropriately marked cells, under the impact of a laser beam focussed on to the hole of the nozzle 4 and which excites the cells.

A pair of conductive plates 64, 66 respectively raised to a high positive voltage and a high negative voltage are located following the electrode E on either side of the cell flux. These plates make it possible to selectively pass said drops, as a function of their charge, into containers 68.

FIG. 5 illustrates a special embodiment of the process according to the invention making it possible to produce an optical analysis device, like device 2 described hereinbefore. In order to produce said device, the initial stage is to produce a nozzle 4 and for this purpose use is made of a thick-walled capillary tube, which is made preferably from glass and is commercially available, such as e.g. a thermometer-type tube. This capillary tube is cut perpendicular to its axis and, by means of a diamond tool, from the two faces of the section obtained are machined two bearing surfaces or cylindro-conical bores 70, 72 along the axis of said section. Machining is carried out in such a way that in the centre of said section is left behind a small portion of the capillary and the conical portions of the two bores converged towards said portion, the latter constituting the microhole of the nozzle.

The optical element 6 referred to hereinbefore is then obtained by the injection moulding of a plastics material with an optical index close to that of glass. This plastics material is e.g. Plexiglas (registered trade mark).

For this purpose, use is made of an appropriately shaped mould, in which the nozzle obtained is accurately positioned.

FIG. 5 diagrammatically shows the mould 74 making it possible to produce device 2. This mould has two half-shells 76, 78 for application to one another along a joining plane 80. It is also possible to see centring pins 82, 84, which are respectively integral with the two half-shells 76, 78. These pins can be inserted into the cylindrical portions of the bores 70, 72 and make it possible to maintain the nozzle in place in the mould. One 76 of the half-shells is also provided with nozzles 86 for the injection of the plastics material and vents 88 permitting the evacuation of gases during injection moulding.

Following the moulding of the optical element 6, device 2 is removed from the mould and polishing can take place at the joint. It is then possible to metallize the dioptric element 12. FIG. 5 shows that the mould is such that following the mould removal of element 6, the latter has shoulders 7, which trap the nozzle 4 on the periphery of the end faces thereof.

In a purely indicative and non-limitative manner, the capillary tube has a roughly 3 mm thick wall, the height of the capillary tube section is approximately 6 mm, the hole 8 has a height of approximately 100 to 120 micrometers and a diameter of approximately 70 micrometers and the conical portions of the bores 70, 72 have an apex semiangle of approximately 45°.

We claim:

1. Process for the production of a device (2) for the optical analysis of a microparticle flux able to emit light, comprising a nozzle (4) made from a material transparent to said light and having a hole (8) therein to provide for the passage of the flux, an optical element (6) moulded around said nozzle, said optical element being made from a material transparent to said light, and having a melting point below that of the nozzle material and with an optical index close to that of said material and having a dioptric element (10) admitting an optical axis passing through the hole.

2. Process according to claim 1, wherein the material from which the optical element (6) is made is a plastics material and said optical element is injection moulded.

3. Process according to claim 1, wherein the dioptric element (10) is spherical and convex.

4. Process according to claim 3, wherein the first Weierstrass point of the spherical dioptric element (10) coincides with the center of the hole (8).

5. Process according to claim 3, further comprising the optical element (6) including, opposite to the spherical dioptric element (10) with respect to hole (8), a spherical convex wall (12), centered on the hole and wherein after producing the device (2), said wall is made optically reflecting.

6. Process according to claim 1, wherein the nozzle (4) is formed by first cutting a capillary tube, by making two bores along the axis of the section obtained with substantially conical bottoms (70, 72) leaving a portion of the capillary, which thus constitutes the said hole (8) and converging towards said portion.

7. Process for the production of a cytofluorimeter comprising: making a device according to the process of claim 1, thereafter assembling the device (2) for the optical analysis of a flux (9) of microparticles such as biological cells or subcellular elements, able to emit light when subject to light excitation, the flux being directed along an axis, with means (36, 40, 42) for forming an exciting light beam of said microparticles and with means for analyzing said light (59, 61).

8. Process according to claim 7, wherein after producing the device (2), said device is made integral with a part (18) having a cavity (22) communicating with the hole (8) of the nozzle (4), said part being made integral with first (24) and second (26) tubes, whereof the respective ends issue into said cavity facing the nozzle, the first tube being provided for the circulation of a microparticle suspension in the direction of said hole, the end of the second tube being further from the hole than the end of the first tube and the second tube serving to circulate a liquid for sheathing the microparticle suspension prior to the passage thereof through the hole.

9. Process according to claim 8, wherein the two tubes (24, 26) are electrically conductive and connected to means (30, 34) provided for the electrical analysis of the cells.

10. Process according to claim 9, wherein the device (2) provided with said part (18) and said tubes (24, 26) is oriented in such a way that the tubes are substantially vertical and positioned lower than the device.

11. Process according to claim 8, wherein the device (2) provided with said part (18) and said tubes (24, 26) is oriented in such a way that the tubes are substantially vertical and positioned higher than the device.

12. Process according to claim 7, wherein the means for forming the exciting light beam have means (40, 42) for the focussing thereof and wherein an inlet face (44) is provided on the optical analysis device (2) for said light beam, positioned in such a way as to permit the passage of the focussed beam into said hole (8) perpendicular to the optical axis of the dioptric element (10) and to the axis of the microparticle flux (9).

13. Process according to claim 12, wherein a light outlet face (16) is provided on the device (2), opposite to the inlet face (14) with respect to the hole (8), and an exciting beam stopping means (44) facing said outlet face is provided, following the interaction of said beam with the microparticle flux, said stopping means being able to allow the passage on either side thereof of a light (46) diffused under small angles by the microparticles.

* * * * *